United States Patent [19]
Whalley

[11] 3,952,064
[45] Apr. 20, 1976

[54] PROCESS FOR PRODUCING MERCAPTOPHENOLS

[75] Inventor: William G. Whalley, Vancouver, Wash.

[73] Assignee: Crown Zellerbach Corporation, San Francisco, Calif.

[22] Filed: July 18, 1974

[21] Appl. No.: 489,625

Related U.S. Application Data

[63] Continuation-in-part of Ser. No. 340,627, March 12, 1973, abandoned.

[52] U.S. Cl............................ 260/609 D; 260/608
[51] Int. Cl.².................................. C07C 149/36
[58] Field of Search...................... 260/608, 609 D

[56] References Cited
UNITED STATES PATENTS

| | | | |
|---|---|---|---|
| 3,468,961 | 9/1969 | Geering et al. | 260/608 |
| 3,479,407 | 11/1969 | Laufer | 260/608 |
| 3,812,192 | 5/1974 | Gabler et al. | 260/608 |

FOREIGN PATENTS OR APPLICATIONS

| | | | |
|---|---|---|---|
| 1,369,616 | 8/1962 | France | 260/608 |
| 2,021,298 | 11/1970 | Germany | 260/608 |

OTHER PUBLICATIONS
J. Chem. Soc. 3876-9 (1962).

*Primary Examiner*—Lewis Gotts
*Assistant Examiner*—D. R. Phillips
*Attorney, Agent, or Firm*—Jerome S. Marger

[57] ABSTRACT

A selective process for producing mercaptophenols is achieved by reducing the polysulfides which result from contacting phenols with sulfur chloride in a polar solvent reaction medium including a hydrogen chloride promoter, wherein the concentration of phenols is relatively dilute. The process selectivity promotes the sulfurization of phenols to polysulfides which are reducible to mercaptophenols.

19 Claims, 1 Drawing Figure

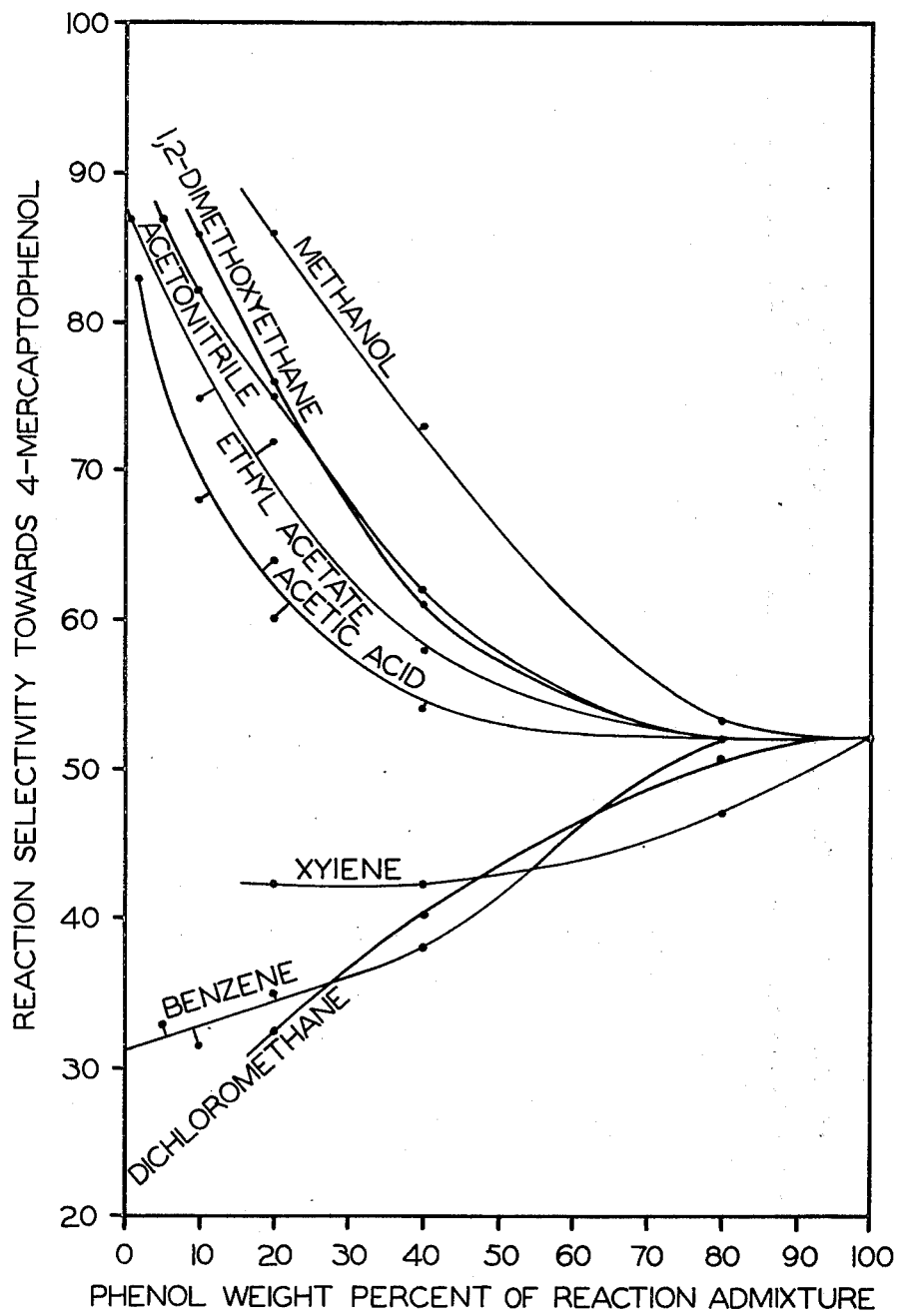

PROCESS FOR PRODUCING MERCAPTOPHENOLS

CROSS REFERENCE TO RELATED APPLICATION

This is a continuation-in-part of U.S. Patent application Ser. No. 340,627, filed Mar. 12, 1973, now abandoned.

BACKGROUND OF THE INVENTION

Efforts have been made to improve the selectivity of the sulfurization of phenols and reduction thereof to mercaptophenols. The sulfurization of phenols has heretofore produced large quantities of impurities such as monosulfides, which are not reducible to mercaptophenols. This lack of process selectivity has also prevented the isolation of high purity mercaptophenols due to the similar physical profiles of the mercaptophenols and side-produced impurities. Known sulfurization processes employing sulfur chloride for the production of phenolic sulfides in which phenolic rings are linked by one or more sulfur atoms continue to be unsatisfactory sources for mercaptophenols. The difficulty is that the action of sulfur chloride on phenols results in mutation reactions and sulfur deposits which constitute mixtures of mono- and poly-sulfides wherein the amount of monosulfide prevails.

Heretofore, efforts to improve the selectivity of the sulfurization of phenols with sulfur chloride and the subsequent reduction to mercaptophenols have been directed to the use of sterically-hindered phenols, and/or variations of catalysts, for example, metal or metal-containing catalysts, solvents, additives, and the like. These efforts not only fail to report on the effect of reducing the concentration of phenols in a reaction admixture, but, in fact, the reported works would direct a conclusion that decreasing the concentration of phenols should produce a slight to marked decrease in yield of polysulfides of phenols which are reducible to mercaptophenols. Furthermore, the use of metal-containing catalysts adds an undesirable component to the reaction system. The additive metal ultimately appears as an unwanted impurity in the product formed thereby requiring additional removal steps to eliminate it from the system. This removal operation is both time-consuming and costly.

I have found that a process having good conversion of phenols coupled with high selectivity for polysulfides, therein providing a desirable source for mercaptophenols, results from a reaction slurry system containing low concentrations of phenols and sulfur chloride, in a polar solvent reaction medium, the slurry including a catalytic amount of hydrogen chloride promoter. Quite surprisingly, I have found that by reducing the concentration of phenols from about 1% to about 25% by weight of the reaction admixture, improved selectivity for polysulfides of phenols reducible to the corresponding mercaptophenols is achieved. However, low concentrations of phenols can cause slower reaction rates. Therefore, a catalytic quantity of a hydrogen chloride promoter is employed in the subject reaction system to increase the rate of selective sulfurization of phenols without introducing impurities to the system caused by the addition of metals or metal-containing catalysts. The reaction admixture containing the reducible polysulfides can be reduced by known methods, for example, the hydrogenating-splitting of polysulfides to mercaptans. The mercaptophenols produced according to this process can be isolated in a relatively high purity form as a direct result of the selectivity of the sulfurization reaction.

Therefore, it is the primary objective of this invention to provide a selective process for the production of mercaptophenols from the sulfur chloride sulfurization of phenols in a reaction slurry containing a polar solvent and a catalytic amount of hydrogen chloride, and the subsequent reduction of the resulting polysulfides. Another objective of this invention is the production and isolation of high purity mercaptophenols by the above described process which controls undesired mutation reactions and sulfur deposits which can result from the uncontroled action of sulfur chloride on phenols.

SUMMARY OF THE INVENTION

The invention relates to a selective process for the preparation of polysulfides of phenols through the action of sulfur chloride on phenols, in a reaction slurry containing a polar solvent and a catalytic amount of HCl, and for the reduction of the sulfides to corresponding mercaptophenols. In another aspect, the invention relates to a process for preparing mercaptophenols with a reduced presence of undesired degradation products common to the action of sulfur chloride on phenols, therein resulting in greater yields and improved purity.

DESCRIPTION OF DRAWING

The FIGURE is a graph depicting the effect of phenol concentration as a weight percent of reaction admixture on the reaction selectivity toward 4-mercaptophenol in various polar and nonpolar solvents. The graph results from the sulfur chloride sulfurization of phenol wherein 59% of the theoretical quantity of sulfur chloride was present. The reaction selectivity is presented as percent yield of 4-mercaptophenol after reduction of the sulfurization products, based on the amount of phenol consumed.

DESCRIPTION OF PREFERRED EMBODIMENTS

Phenols as defined for the purpose of this invention may include any of those having the formula:

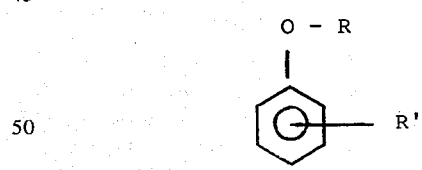

wherein R is selected from hydrogen, alkyl, cycloalkyl, haloalkyl groups, and combinations thereof, having from 0 to about 10 carbon atoms per R group; R' is either $R''_n$ or H, $R''_n$ being selected from hydroxyl, halogen, alkyl, alkoxy, cycloalkyl, and combinations thereof, and having a total of from 1 to 5 carbon atoms contained in all of the carbon-containing R'' groups substituted on said phenolic ring, and n is an integer of from 1 to 2. Examples of these phenols include phenol, cresols, resorcinol, catechol, hydroquinone, xylenols, 2-chlorophenol, 3-chlorophenol, 2-bromophenol, and the like. The phenols may be used in the pure form or as mixtures, depending on the desired mercaptophenols which result from the process.

The preferred sulfur chloride is sulfur monochloride; however, mixtures of various sulfur chlorides may also be used.

The process of the present invention utilizes a polar solvent reaction medium. THe same solvent is generally used for carrying reactants into contact; however, a large number of polar solvents may be used in the process. For purposes of this invention, a polar solvent is defined as that solvent which has a solubility in water of at least 2.0 based on grams of solvent dissolved per 100 grams of water at a temperature of approximately 25° C. The following exemplary solvents and their respective solubilities in water illustrate a division of polar from nonpolar solvents for the purpose of this invention at about 2.0. These exemplary solvents which are suitable and nonsuitable according to the invention as demonstrated in the FIGURE, are listed as follows:

| Solvent[1] | Grams Solvent Dissolved 100 Grams Water at about 25° C. |
|---|---|
| Methanol | ∞ |
| Acetonitrile | ∞ |
| 1,2-dimethoxyethane | ∞ |
| Acetic Acid | ∞ |
| Ethyl Acetate | 8.1 |
|  | ↑ Polar |
| --- | 2 --- |
|  | ↓ Nonpolar |
| Xylene | 0.02 |
| Benzene | 0.18 |
| Dichloromethane | 1.30 |

[1]Water Solubility taken from tables of physical properties of Solvents, A. Weissberger, E. S. Proskauer, J. A. Riddick, E. E. Toops, Jr., "Organic Solvents", Interscience Publishers, Inc., New York, 1955, pp 47–258

It is possible to use polar solvents which in themselves react with sulfur chloride, provided, that these reactions are considerably slower than the sulfurization of phenols according to the invention. However, such an interaction between the polar solvent and sulfur chloride should be avoided in order to minimize reagent losses due to side reactions.

The selective sulfurization of phenols with sulfur chloride according to the invention is promoted by the presence of catalytic quantities of hydrogen chloride in the reaction slurry. More specifically, the sulfurization of phenols with sulfur chloride generally proceeds at a substantially reduced reaction rate without the addition of hydrogen chloride promoter to the slurry although a catalytic amount of HCl is eventually formed in situ after the passage of a substantial period of time. Therefore, in order to avoid the unwanted induction time period which results prior to reacting the HCl level required to catalyze the phenol-sulfur chloride reaction, when an in situ phenol-SCl reaction is employed, a reaction slurry comprising a phenolic compound, as previously described, sulfur chloride, a polar solvent, and a catalytic amount of hydrogen chloride is first formed. In general, the hydrogen chloride promoter is present in an amount of at least 0.1% by weight of the reaction admixture. The in situ-produced hydrogen chloride can be continuously removed or removed with the solvent medium after reaction completion.

The sulfurization of the phenols with sulfur chloride is preferably carried out in a temperature range of about −50° C. to about 150° C., particularly −20° C. to 100° C. The pressure does not have any significant effect on the reaction; thus, for economic reasons, the reaction is generally carried out at atmospheric pressure. However, higher than atmospheric pressures may be used wherein volatile catalysts and/or solvents are present in order to retain these substances in the reaction admixture, thus allowing for higher reaction temperatures when necessary. The proportions in which the various components are introduced into the reaction admixture may vary; however, the concentration of reactive phenols has been defined according to the invention to constitute less than about 25% by weight of the reaction admixture.

The sulfur chloride is contacted with phenols in at least a 0.1 stoichiometric quantity based on phenols concentration. The stoichiometric quantity is one mole of sulfur chloride for every two moles of the phenol. Stoichiometric quantities of sulfur chloride of up to about 1.5 of the theoretical quantity can be used. The preferred concentration of phenols comprises from about 1% to about 25% by weight of the reaction admixture, with polar solvent reaction medium constituting the major portion of the reaction admixture. As illustrated in the FIGURE, lowering of the concentration of phenol in a polar solvent improves selectivity for polysulfides reducible to 4-mercaptophenol. The FIGURE also illustrates that the lowering of phenol concentration improves selectivity only when polar solvents are utilized. Nonpolar solvent reaction medium demonstrates an increase in selectivity according to the FIGURE only when the concentration of phenol is increased; therefore, the nonpolar solvents do not satisfy the requirements of a reaction medium according to the invention.

The sulfurization reaction of the process preferably is carried out in such a manner that all the reaction components can react with each other more or less simultaneously. This may be achieved, for example, by first introducing the phenols or phenolic compounds (if desired, in the polar solvent and with the promoter) into a reaction vessel, and then adding sulfur chloride. Another approach could be introducing the sulfur chloride with or without polar solvent carrier into the reaction vessel and then adding the dilute phenol-polar solvent solution. Preferably, the same polar solvent is used as carrier and as reaction medium regardless of the choice of contacting sequence.

The reaction admixture may be treated by known physical and/or chemical methods in order to reduce the reaction admixture and to separate and purify the resulting mercaptophenols. The order and content of these purification steps do not lend themselves to a fixed order of standard procedures due to the wide variety of polar solvents, catalysts and phenols, to which this invention is applicable. Isolation methods may include removal of in situ-produced hydrogen chloride by the action of heat, vacuum, extraction, neutralization, or by inert gas purge, and the like. The polar solvent reaction medium may be removed by similar means to the extent desired. Depending on the process conditions and/or the phenolic reagent, the phenolic polysulfide intermediates can be separated from the reaction mixture by extraction and/or crystallization means. However, the reaction admixture may be subjected to the reduction step before or after any combinations of the above separation steps and thereafter subjected to any of several separation steps including extraction, distillation, crystallization, precipitation, and the like.

A particular embodiment of the process consists in carrying it out continuously. This may be done, for example, by pumping the phenols, a polar solvent and a hydrogen chloride promoter, through a reactor into which the required quantity of sulfur chloride is added.

The sulfurization products are removed continuously from the reaction chamber for reduction and isolation. If the reactor is suitably constructed, the reactants will be sufficiently contacted as a result of the flow conditions. Both in the intermittent and in the continuous process, it may be advantageous to carry out the reaction in a stream of inert gas so that the in situ-found hydrogen chloride can be removed continuously from the reaction admixture.

The polysulfides of phenols obtained by the selective sulfurization of phenols according to the invention can be reduced to the mercaptophenols by several known methods. These typically include the action of metals in acid (nascent hydrogen), catalytic hydrogenation, electrochemical reduction, chemical reduction, and the like.

Catalytic hydrogenation is one preferred method of reducing the polysulfides produced, according to the invention, to mercaptophenols. The reaction admixture is heated to remove hydrogen chloride and excess polar solvent and is then subjected to the action of hydrogen at a pressure of about 100 to about 2,000 pounds per square inch at a temperature of about 100° C. to about 190° C. in the presence of a hydrogenation catalyst. Hydrogenation catalysts typically include, for example, metals of Group VIII and a very large number of alloys and compounds thereof.

Another preferred method of reducing the polysulfides according to the invention is contacting the reaction admixture after hydrogen chloride removal with a solution of excess sodium mercaptide and sodium hydroxide at a temperature of from about 0° C. to about 100° C. The by-product, dimethyl disulfide, may be separated by distillation, decantation or extraction, and the mercaptophenols recovered by acidification, decantation or extraction, and distillation.

In general, the isolation of the high purity mercaptophenols may be achieved several ways. The treatment of the reaction mixture, both before and after the reduction step in order to recover high purity mercaptophenols, will depend upon the selected reduction method and the specific properties of the mercaptophenol and side-produced products. All isolation techniques suitable according to the method of the invention are accepted chemical procedures which can be followed with proper regard to the above conditions and the specific properties of the solvent used.

Hydrogen chloride produced in situ may be removed, if desired, by evaporation and/or distillation, stripping, with an inert gas, or neutralized with a base. The solvent may be removed, if desired, by distillation at atmospheric or reduced pressure, for example, by converting the reaction products to water-soluble salts, with aqueous sodium hydroxide, followed by decantation or distillation of the solvent.

If the reaction admixture product is in the form of a salt after reduction, an acidification-decantation or an acidification-extraction sequence may be used for isolation. The reaction mixture after the reduction step is or may be easily converted to a mixture of unreacted starting phenols, the desired mercaptophenols, and its isomers, chlorinated by-products and various thiodiphenol isomers. The proportions of these products will depend upon the starting phenol and the reaction conditions. The isolation steps necessary to obtain a sufficient degree of purity in the final mercaptophenol depends upon the purity desired and the specific nature of the product. Suitable isolation techniques, for example, crystallization, and/or fractional distillation may be used according to the invention and are exemplified by the following combinations:

1. The sulfurization reaction admixture is stripped of solvent and hydrogen chloride, and the admixture is then catalytically hydrogenated, with the mercaptophenols being isolated by distillation means;
2. The sulfurization reaction admixture is stripped of solvent and hydrogen chloride, and the admixture is then reduced by a sodium mercaptide mixture which is thereafter acidified, with the resulting mercaptophenols being isolated through distillation means; and
3. The sulfurization reaction admixture having, for example, acetic acid as the polar solvent, is reduced with a metal such as zinc, and the results are neutralized and filtered, with the mercaptophenols being isolated through distillation means.

For exemplary purposes, the inventive process can be illustrated specifically by referring to the reaction of phenol with sulfur monochloride in the presence of anhydrous hydrogen chloride promoter. In addition, the polar solvents, as illustrated in the FIGURE, can be applied as the reaction medium with the resulting production of 4-mercaptophenol being in high yield due to the selectivity of the sulfurization of phenol.

The data as found in Table I hereinbelow supports the graphic illustration of the FIGURE. The graph illustrates the effect of phenol concentration on selectivity as to mole percent yield of 4-mercaptophenol based on phenol consumed in various solvents. Dilute phenol contained in the various solvents was contacted with sulfur monochloride (59% of the stoichiometric quantity) in the presence of hydrogen chloride promoter. The hydrogen chloride was added to the phenol-solvent before the addition of sulfur monochloride. The sulfurization reaction admixture was reduced and the results analyzed by gas-liquid chromatography (GLC) methods with the following results:

Table I

Selectivity[1] for products reducible to 4-mercaptophenol based on consumed phenol

| Solvent | Concentration of Phenol % by Weight of Reaction Admixture | | | | |
|---|---|---|---|---|---|
| | 80% | 40% | 20% | 10% | 5% |
| Benzene | 53 | 39 | 35 | 32 | 33 |
| Xylene | 47 | 43 | 44 | — | — |
| Dichloromethane | — | 40 | 34 | — | — |
| Ethyl Acetate | — | 58 | 72 | 75 | 87 |
| Acetonitrile | 50 | 63 | 75 | — | 86 |
| 1,2-dimethoxyethane | — | 61 | 76 | 86 | — |
| Methanol | 53 | 74 | 85 | — | — |
| Acetic Acid | — | 54 | 60,64 | 68 | — |

[1]% Selectivity = $\frac{\text{(moles of phenol appearing as 4-mercaptophenol after reduction)} \times 100}{\text{moles of phenol consumed in reaction after reduction}}$ All analyses of this invention were performed on a gas chromatograph with a 5′ × ¼″ 3% SE.30 on 100-120 Var-a-Port 30 column and a helium flow rate of 60 ml per minute. The temperature was linearly programed from 100° C. to 250° C. at 20 degrees per minute and held at 250° C. until analysis was complete. All analytical values are corrected for detector response to the individual compounds.

Example 1 below demonstrates that the percent selectivity and percent conversion are substantially the same when a sulfurization reaction slurry is formed by admixing a catalytic amount of hydrogen chloride with a low concentration of phenol, sulfur dichloride, and a polar solvent, or by allowing a catalytic amount of hydrogen chloride to be generated in situ over an extended period of time which eventually produces the desired selectivity and conversion.

However, by providing for the addition of the requisite catalytic amount of hydrogen chloride promoter to be initially present in the subject reaction slurry, a substantial increase in the reaction rate will ensue. Therefore, by providing for additions of a catalytic amount of hydrogen chloride promoter when the sulfurization slurry is formed, a substantial decrease in the reaction time, because of the substantial increase in the reaction rate, will be provided herein.

For the purpose of this invention, percent selectivity and percent conversion are defined, for example, in the case of phenol and 4-mercaptophenol, as follows: Percent selectivity is defined by dividing the moles of phenol appearing as 4-mercaptophenol after quantitative reduction by the moles of phenol consumed in the reaction and multiplying the result by 100; and percent conversion is defined by dividing the moles of phenol consumed in the reaction by the moles of phenol added to the reaction and multiplying the results by 100. The stoichiometric quantity of sulfur monochloride is defined as one mole for each two moles of phenol.

EXAMPLE 1

A solution containing 2 moles of phenol per liter of acetic acid was divided into two parts. One part was saturated with hydrogen chloride, then one-half the stoichiometric amount of sulfur dichloride was added to each part. The solutions were allowed to react and the mixtures were analyzed by GLC after reduction. In the case of no initial hydrogen chloride additive, the conversion was 96% of theoretical and the selectivity was 61%. In the case of saturation with hydrogen chloride, conversion was 94% of theoretical and selectivity was 64%.

A 10% by weight solution of phenol (0.532 mole) in ethyl acetate was prepared and combined with various percentages of hydrogen chloride (see Table II). In each case, ethyl acetate was added so that the total solution weight of the phenol, ethyl acetate, and HCl was 500 grams. The solutions were placed in a one-liter round bottom flask equipped with a magnetic stirrer and thermometer and the flask placed in a well-insulated container. While stirring at initial temperature of 23°–24° C., 21.2 ml of sulfur monochloride were added to the ethyl acetate solution.

The reaction temperature was monitored with respect to time, it being assumed that sulfurization reaction was substantially completed at a point in time when a maximum temperature rise was observed. The maximum temperature for a given hydrogen chloride concentration varied with the amount of hydrogen chloride which was allowed to escape from the solution. For example, in an open-flask system the maximum temperature rise was about 12° C. However, when the flask was stoppered, the temperature of about 17° C. occurred before the stopper became loose.

As indicated in Table II below, a 10% hydrogen chloride solution, based on the total weight of the sulfurization slurry, reached a maximum temperature after 7 to 8 minutes. Moreover, 5% and 2.5% hydrogen chloride solutions reached their maximum temperatures after 35 and 70 minutes, respectively. However, when no hydrogen chloride was initially added, a period of 360 minutes was required for enough in situ hydrogen chloride to be produced to cause a maximum temperature rise to be reached. Therefore, 5- to 50-fold increases in reaction time and, in turn, in reaction rate, can be realized by initially adding catalytic amounts of hydrogen chloride to the subject reaction slurry.

Table II

| Percent HCl | Maximum Temperature Rise | Time to Reach Maximum Temperature |
|---|---|---|
| 0 | 13.8° C. | 360 minutes |
| 2.5 | 19.8° C. | 70 minutes |
| 5.0 | 20° C. | 35 minutes |
| 10.0 | 12° C. | 7–8 minutes |

The minimal effect on percent selectivity and percent conversion of varying the stoichiometric amount of sulfur monochloride (10% and 90%) is demonstrated in Example 2.

EXAMPLE 2

A solution containing 2 moles of phenol per liter of acetic acid was saturated with hydrogen chloride and divided into two parts. To one part was added 10% of the stoichiometric quantity of sulfur monochloride, and to the other part, 90% of the stoichiometric quantity of sulfur monochloride. After reduction and analysis, the selectivity of the first sample was 56%, while in the second sample the corresponding selectivity was 62%.

The results of Example 2 demonstrate that varying the stoichiometric quantity of sulfur monochloride had little or no effect on the selectivity. The results of Example 2 further demonstrate that the graph as illustrated in the FIGURE, wherein 59% stoichiometric quantity of sulfur monochloride was contacted with phenol, represents a valid analogy wherein decreasing phenol concentration in a polar solvent, according to the invention, substantially improves the selectivity for 4-mercaptophenol.

Example 3, following, demonstrates a specific embodiment of the invention wherein high selectivity and isolation of high absolute yield of 4-mercaptophenol is achieved from reaction of phenol with sulfur monochloride in an ethyl acetate medium.

EXAMPLE 3

Fifty grams of phenol in one liter of ethyl acetate were contacted with hydrogen chloride for a period of from 5 to 10 minutes. Thirty-six grams of sulfur monochloride were added to the phenol, hydrogen chloride, and ethyl acetate. The admixture was allowed to stand at room temperature overnight. The solvent was removed by distillation and residual solvent was removed by steam distillation from the admixture. A total of 985 ml (98%) of the solvent was recovered. Five hundred ml of a solution containing 2.5 moles per liter sodium hydroxide and 1.7 moles per liter of methanethiol in water were added to the residue. The mixture was distilled to recover 27 ml of dimethyl disulfide (theoretical amount). The mixture was cooled, acidified with concentrated hydrochloric acid and extracted with ether. Removal of the ether and distillation of the residue under vacuum (2 mm) gave the following distillate. Analysis showed that the distillate contained 40.3 grams of 4-mercaptophenol and 4.7 grams phenol. The isolated yield was, therefore, 67%. By fractional distillation under reduced pressure a product containing more than 99% 4-mercaptophenol may be prepared.

The following Example 4 demonstrates the process according to the invention utilizing a substituted phenol.

EXAMPLE 4

2,4-dimethylphenol (24.4 grams) and 26 grams of hydrogen chloride were dissolved in 200 grams of 1,2-dimethoxyethane and the solution was combined with 13.5 grams of sulfur monochloride. The temperature of the reaction mixture rose from 20° C. to 30° C. within five minutes. After 1.5 hours, the hydrogen chloride and solvent were removed to yield 35.8 grams of yellow oil. (Theoretical yield was 30.6 grams; the oil contained residual solvent.) GLC analysis after reduction showed that the conversion of 2,4-dimethylphenol to products was 79% and the selectivity of the reaction toward 6-mercapto-2,4-dimethylphenol was 82%. The 6-mercapto-2,4-dimethylphenol was identified by conversion to the 2,4-dinitrophenyl thio ether derivative.

The process according to the invention has produced high selectivity as illustrated in Example 3 wherein phenol with open reactive sites was used as a reagent. Example 4 demonstrates that the substituted phenol, 2,4-dimethylphenol with the para-position closed, resulted in a high selectivity for the corresponding mercaptophenol.

Examples 5–9 hereinbelow further demonstrate that substituted phenols support the resulting improved selectivity for corresponding mercaptophenols when the process according to my invention is utilized. Examples 6 and 8 are not according to my invention and are for comparison with Examples 7 and 9 which are in accordance with the invention. The position of sulfurization of phenols is known to favor para- over ortho-; however, Examples 4, 5, 7, and 9 provide results which show that improved selectivity is achieved with both para- and ortho-substituted phenols when my process is utilized. Example 7 further illustrates that anisole with a substituted oxygen responds with improved selectivity according to the process of my invention.

EXAMPLE 5

24.4 grams of 2,6-dimethylphenol were dissolved in 200 ml of ethyl acetate and 25 ml of ethyl acetate saturated at room temperature with hydrogen chloride. To this solution 13.5 grams of sulfur monochloride were added and the mixture was allowed to stand for 2 hours and 15 minutes. The hydrogen chloride and solvent were removed and the residue was reduced and analyzed. The conversion was 86% with a selectivity for 4-mercapto-2,6-xylenol of 70%.

EXAMPLE 6

To a mixture of 21.6 grams anisole, 21.1 grams 1,2-dimethoxyethane, and 2.7 grams hydrogen chloride at a temperature of 40° C. were added 13.5 grams of sulfur monochloride. The mixture was allowed to stand for 12 hours and the solvent and hydrogen chloride were removed. Analysis of the mixture showed a selectivity toward 4-mercaptoanisole of 61%. Anisole comprised 37% by weight of the reaction admixture.

EXAMPLE 7

To a mixture of 21.6 grams anisole, 213 grams 1,2-dimethoxyethane, and 19.1 grams hydrogen chloride at a temperature of 49° C. were added 13.5 grams of sulfur monochloride. The reaction admixture was allowed to stand for 12 hours and the solvent and hydrogen chloride were removed. Reduction of the reaction mixture showed a selectivity toward 4-mercaptoanisole of 84%. The 4-mercaptoanisole was identified by methylation and comparison with authentic 4-(methylthio)anisole. Anisole comprises 8.1% by weight of the reaction mixture.

EXAMPLE 8

To a mixture of 22.0 grams of catechol, 21 grams of 1,2-dimethoxyethane, and 2.8 grams of hydrogen chloride at a temperature of 40° C. were added 13.5 grams of sulfur monochloride over the space of 3–4 minutes. The mixture became black and exothermic to the point of boiling, and the reaction appeared to be over almost instantaneously. The solvent and hydrogen chloride were removed, and the mixture reduced. By GLC, 4-mercaptocatechol comprised 20% of the product mixture. Catechol comprised 37% of the reaction mixture.

EXAMPLE 9

To a mixture of 22.0 grams catechol, 214.9 grams 1,2-dimethoxyethane, and 21.0 grams hydrogen chloride at an initial temperature of 52° C. were added 13.5 grams of sulfur monochloride. Within 1–2 minutes the temperature increased to 65° C. and began to fall. After 10 minutes the solvent and hydrogen chloride were removed on a rotary evaporator to leave 42 grams of dark yellow oil. By GLC, the 4-mercaptocatechol was found to be 39% of the reaction mixture. Catechol comprised 8.1% of this reaction mixture.

Examples 10 and 11 included hereinbelow present an analogy of the sulfurization of phenols in polar solvents. However, these examples do not include the important feature of my inventive process of utilizing a phenols concentration of about 25% by weight, or less, based on the weight of the sulfurization reaction admixture. Example 12 is according to my inventive process and the tabulated results as found in Table III below fully demonstrate the superior selectivity accordingly wherein Examples 10, 11, and 12 are compared as to percent conversion and percent selectivity.

EXAMPLE 10

20.6 grams of phenol in 23.4 grams dry acetonitrile and 0.005 grams iron powder were combined and purged with nitrogen and stirred. 6.8 grams of sulfur monochloride in 15.6 grams of dry acetonitrile were added drop-wise at −30° C. to −40° C. to the mixture. After the addition, the mixture was stirred at room temperature for 19 hours; the hydrogen chloride and acetonitrile were removed on a rotary evaporator; no crystals formed so the mixture was extracted with ether several times. The combined ether solutions gave the following analysis: Selectivity was 45.9%; conversion, 45.7%.

EXAMPLE 11

The reaction of Example 10 was repeated except that 14.8 grams (the stoichiometric quantity) of sulfur monochloride were used. The reaction admixture was stirred for 18 hours and prepared for analysis as in Example 10, resulting in a selectivity of 43.9% and a conversion of 95.0%.

EXAMPLE 12

9.4 grams phenol, 9.0 grams anhydrous hydrogen chloride and 163 grams of dry acetonitrile were mixed.

6.8 grams (the stoichiometric quantity) of sulfur monochloride were added thereto with stirring. The admixture turned orange in color and the temperature rose from room temperature to 40° C. Within 5 minutes the reaction admixture was light yellow and after 20 minutes the hydrogen chloride and solvent were removed on a rotary evaporator, leaving an admixture of yellow crystals and oil. The admixture was dissolved in ether and analyzed with a resulting selectivity of 86.4% and a conversion of 87.7%.

Table III

| | Analysis[1] | |
|---|---|---|
| | % Conversion[2] | % Selectivity[3] |
| Example 10 | 45.7 | 45.9 |
| Example 11 | 95.0 | 43.9 |
| Example 12 | 87.7 | 86.4 |

[1]All analyses were performed on a gas chromatograph with a 5' × ¼" 3% SE.30 on 100-120 Var-a-Port 30 column and a helium flow rate of 60 ml per minute. The temperature was linearly programed from 100° C. to 250° C. at 20 degrees per minute and held at 250° C. until analysis was complete. All analytical values are corrected for detector response to the individual compounds.
[2]Moles of phenol converted to products × 100 divided by total moles of phenol.
[3]Moles of phenol as 4-mercaptophenol × 100 divided by total moles of phenol in products.

Table III additionally illustrates that conversion does not affect selectivity (Examples 10 and 11). EXamples 1–12 have also demonstrated that high selectivity shown for one specific phenol does not transfer to other phenols unless the process according to my invention is utilized.

EXample 13 below illustrates a reduction in selectivity when the phenol concentration is increased beyond the features of my invention and when the polar solvent reaction medium is absent.

EXAMPLE 13

94 grams phenol were placed in a flask and stirred while hydrogen chloride was added. The mixture was warmed to 60° C. and stirred while 50.6 grams (0.75 stoichiometric quantity) of sulfur monochloride was added during a 6-minute period. After 2 more minutes of stirring, a sample was taken and analyzed to give a selectivity of 50.2% in a conversion of 60.7%.

Example 14, below, demonstrates the effect of increasing the phenol concentration on selectivity and conversion. The effect of in situ-produced hydrogen chloride promoter on reaction rate is also illustrated.

EXAMPLE 14

280 grams of 1,2-dimethoxyethane and 48 grams of phenol were combined and 20 grams of sulfur monochloride were added with mixing. The reaction turned dark brown and the temperature rose to 57° C. within 45 minutes. After 20 hours, the mixture was sampled and 47 grams of phenol and 33.8 grams of sulfur monochloride were added. Within 5 minutes the temperature rose to 55° C. and after 10 minutes another sample (No. 2) was taken and 47 grams of phenol and 33.8 grams of sulfur monochloride were added. The reaction appeared to be complete in two minutes and cooling with a water bath was necessary to prevent hydrogen chloride loss. Sample No. 3 was taken and the remaining mixture was distilled to a pot temperature of 120° C. to remove the hydrogen chloride and some of the solvent. The residual was poured into 1.3 liters of 1.7 molar sodium mercaptide prepared by adding methyl mercaptan to a solution of 2.5 molar sodium hydroxide. The organic layer containing dimethyl disulfide was decanted and the mixture distilled to remove remaining dimethyl disulfide, water, and dimethoxyethane to a pot temperature of 100° C. The admixture was acidified with concentrated hydrochloric acid, the organic layer separated and was washed with sodium bicarbonate and water, and the residue (190.5 grams) was dried, divided in half, and one-half distilled at 0.5 millimeter mercury to yield 42.5 grams of distillate containing (GLC) 39 grams of 4-mercaptophenol. The 39 grams of 4-mercaptophenol represent a 41% isolated yield.

In summary, the analysis of Samples 1, 2, and 3 yielded selectivities of 79.4, 72.3, and 65.7% respectively, thus, again, demonstrating diminishing selectivity with increasing concentration of phenol in a polar solvent-sulfurization process.

The foregoing examples have demonstrated the features of the inventive process, particularly the relationship between selectivity and the concentration of phenol reactants in a polar solvent. Criticality of high selectivity of the inventive process for phenol concentrations of about 1% to about 25% by weight of the reaction admixture is also demonstrated by the examples as well as the illustration of the FIGURE. Substituted phenols have been shown to support the critical features of the process as well as the exemplary phenol reaction to produce 4-mercaptophenol. Ambient temperatures and pressures have been demonstrated to be suitable while hydrogen chloride promoter has been found to increase the reaction rates. The criticality of polar solvent as defined according to the invention and the phenol concentration therein has been clearly demonstrated.

Reasonable variations and modifications of this invention can be made, or followed, in view of the foregoing disclosure without departing from the spirit and scope thereof.

What I claim is:

1. A process for the preparation of mercaptophenols, including a selective sulfurization reaction, comprising the steps of
   a. forming a sulfurization reaction system including at least one phenol compound, a sulfur chloride, a polar solvent reaction medium having a water solubility of at least about 2.0, and a catalytic amount of hydrogen chloride promoter, said phenolic compounds having a formula

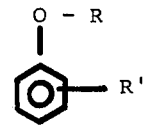

wherein R is selected from the group consisting of hydrogen, alkyl, cycloalkyl, haloalkyl, and combinations thereof, the carbon-containing R groups having from 1 to about 10 carbon atoms, and R' is either R''$_n$ or H, R'' being selected from the group consisting of hydroxyl, halogen, alkyl, alkoxy, cycloalkyl, and combinations thereof, the carbon-containing R'' groups having a total of from 1 to 5 carbon atoms, n being an integer from 1 to 2, said phenol forming less than about 25% by weight of the total sulfurization system, said sulfur chloride being present in at least a 0.1 stoichiometric quantity based on the concentration of said phenol, said polar solvent reaction medium including those polar solvents which themselves react with said sulfur chloride, provided that said polar solvent-sulfur chloride reaction is considerably slower than said selective sulfurization reaction, said hydrogen chloride promoter being present in an amount of at least 0.1% by weight based on the weight of the total sulfurization reaction system;

b. reacting said phenol and sulfur chloride to form a polysulfide; and c. reducing the polysulfide to form said mercaptophenol.

2. The process of claim 1, wherein the polar solvent used is one that avoids said polar solvent-sulfur chloride interaction in order to minimize reagent losses due to side reactions.

3. The mercaptophenol-formation process of claim 1, wherein the sulfurization reaction system is saturated with hydrogen chloride.

4. The mercaptophenol-formation process of claim 1, wherein the phenolic compounds employed in the sulfurization reaction system are selected from the group consisting of phenol, cresols, resorcinol, catechol, hydroquinone, xylenols, 2-chlorophenol, 3-chlorophenol, and 2-bromophenol.

5. The mercaptophenol-formation process of claim 1, wherein the phenolic compound employed in the sulfurization reaction system is phenol.

6. The process according to claim 1, adapted for continuously producing mercaptophenols, wherein the sulfurization products are formed and removed continuously from the reaction system for subsequent reduction thereof.

7. The process of claim 1, wherein said polar solvent reaction medium is selected from the group consisting of 1,2-dimethoxyethane, acetic acid, ethyl acetate, acetonitrile, and methanol.

8. The process of claim 1, which further includes the step of isolating said mercaptophenol produced.

9. The mercaptophenol-formation process of claim 1, wherein said catalytic amount of hydrogen chloride promoter is added initially in forming the sulfurization reaction system, thus providing an increase in the sulfurization reaction rate.

10. The mercaptophenol-formation process of claim 1, wherein the sulfur chloride is added in stoichiometric quantities up to about 1.5 of the theoretical quantity.

11. The mercaptophenol-formation process of claim 1, wherein the sulfur chloride is sulfur monochloride.

12. The mercaptophenol-formation process of claim 1, wherein the reduction step is comprised of catalytic hydrogenation.

13. A process for the preparation of 4-mercaptophenol, in a selective sulfurization reaction, comprising the steps of a. forming a sulfurization reaction system including phenol, sulfur monochloride, a polar solvent reaction medium having a water solubility of at least about 2.0, and a catalytic amount of hydrogen chloride promoter, said phenol forming from up to about 25% by weight of the total sulfurization system, said sulfur monochloride being present in at least a 0.1 stoichiometric quantity based on the concentration of phenol, said polar solvent reaction medium including those polar solvents which themselves react with said sulfur chloride, provided that said polar solvent-sulfur chloride reaction is considerably slower than said selective sulfurization reaction, said hydrogen chloride promoter being present in an amount of at least 0.1% by weight based on the weight of the total sulfurization reaction system;

b. reacting phenol and sulfur monochloride to form polysulfides; and c. reducing the polysulfides to form said mercaptophenol.

14. The process of claim 13, wherein the polar solvent used avoids said polar solvent-sulfur monochloride interaction in order to minimize reagent losses due to side reactions.

15. The 4-mercaptophenol-formation process of claim 13, wherein the sulfurization reaction system is saturated with said hydrogen chloride promoter.

16. The process according to claim 13, adapted for continuously producing 4-mercaptophenol, wherein the sulfurization products are formed and removed continuously from the reaction system for reduction thereof.

17. The 4-mercaptophenol-formation process of claim 13, wherein said catalytic amount of hydrogen chloride promoter is added initially in forming the sulfurization reaction system, thus providing an increase in the sulfurization reaction rate.

18. The mercaptophenol-formation process of claim 13, wherein the sulfur monochloride is used in stoichiometric quantities up to about 1.5 of the theoretical value.

19. The process of claim 13, wherein the polar solvent reaction medium is selected from the group consisting of 1,2-dimethoxyethane, acetic acid, ethyl acetate, acetonitrile, and methanol.

* * * * *